United States Patent
Weisbeck et al.

(10) Patent No.: US 6,603,028 B1
(45) Date of Patent: Aug. 5, 2003

(54) METHOD FOR OXIDIZING HYDROCARBONS

(75) Inventors: Markus Weisbeck, Köln Holweide (DE); Ernst Ulrich Dorf, Krefeld (DE); Gerhard Wegener, Mettmann (DE); Christoph Schild, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/762,179

(22) PCT Filed: Jul. 27, 1999

(86) PCT No.: PCT/EP99/05370

§ 371 (c)(1),
(2), (4) Date: Mar. 23, 2001

(87) PCT Pub. No.: WO00/07964

PCT Pub. Date: Feb. 17, 2000

(30) Foreign Application Priority Data

Aug. 7, 1998 (DE) .......................... 198 35 481

(51) Int. Cl.[7] .................. C07D 301/10; B01J 23/48; B01J 23/50
(52) U.S. Cl. .................. 549/536; 549/534; 502/347; 502/350
(58) Field of Search ................ 549/534, 536; 502/347, 350

(56) References Cited

U.S. PATENT DOCUMENTS

| 3,836,436 | A | 9/1974 | Rivola et al. ................. 204/10 |
|---|---|---|---|
| 4,410,501 | A | 10/1983 | Taramasso et al. ......... 423/326 |
| 4,833,260 | A | 5/1989 | Neri et al. ................... 549/531 |
| 5,173,469 | A | 12/1992 | Wunde et al. ............... 502/340 |
| 5,221,795 | A | 6/1993 | Clerici et al. ................ 549/531 |
| 5,281,728 | A | 1/1994 | Wunde et al. ............... 549/537 |
| 5,623,090 | A | 4/1997 | Haruta et al. ................ 568/360 |
| 5,656,249 | A | 8/1997 | Yoshida et al. ........... 423/239.1 |
| 5,668,077 | A | 9/1997 | Klopries et al. ............. 502/347 |
| 5,703,254 | A | 12/1997 | Gaffney et al. .............. 549/536 |
| 5,714,432 | A | 2/1998 | Yoshida et al. .............. 502/415 |
| 5,734,068 | A | 3/1998 | Klopries et al. ............. 549/536 |
| 5,760,254 | A | 6/1998 | Grey ........................... 549/532 |
| 5,763,630 | A | 6/1998 | Kahn et al. .................. 549/534 |
| 5,772,973 | A | 6/1998 | Yoshida et al. ........... 423/239.1 |
| 5,801,117 | A | 9/1998 | Yoshida et al. .............. 502/415 |
| 5,965,754 | A | 10/1999 | Clark et al. .................. 549/533 |
| 6,031,116 | A | 2/2000 | Bowman et al. ............. 549/523 |

FOREIGN PATENT DOCUMENTS

| EP | 0 179 584 | 3/1992 |
|---|---|---|
| EP | 709 360 | 5/1996 |
| JP | 4-352771 | 12/1992 |
| WO | 96/23023 | 1/1996 |
| WO | 97/25143 | 7/1997 |
| WO | 97/47386 | 12/1997 |
| WO | 98/00414 | 1/1998 |
| WO | 98/00415 | 1/1998 |
| WO | 99/00188 | 1/1999 |

OTHER PUBLICATIONS

CatalysisReviews: Science and Engineering,23 (1&2) (month unavailable)1981,pp. 127–149, W.M.H. Sachtler, C. Backx and R.A. Van Santen, On the Mechanism of Ethylene Epoxidation.

*Primary Examiner*—Ba K. Trinh
(74) *Attorney, Agent, or Firm*—Joseph C. Gil; John E. Mrozinski, Jr.

(57) ABSTRACT

The invention relates to a method for oxidizing hydrocarbons with a hydrogen/oxygen mixture in the presence of a catalyst. The catalyst contains a) a support material which contains titanium and b) silver particles having an average particle size ranging from 0.3 to 100 nm.

2 Claims, No Drawings

METHOD FOR OXIDIZING HYDROCARBONS

This application is a 371 of PCT/EP99/05370, filed Jul. 27, 1999.

The present invention relates to a process for the oxidation of hydrocarbons on a catalyst containing silver in the presence of a hydrogen/oxygen mixture.

The direct oxidation of ethene to ethene oxide by molecular oxygen is well known and is used commercially to produce ethene oxide. The typical catalyst for this application contains metallic or ionic silver, optionally further modified with different promoters and activators. Most of these catalysts contain a porous, inert catalyst support with small surfaces such as alpha aluminium oxide, for example, onto which silver and promoters were applied. A review of the direct oxidation of ethene in the presence of supported silver catalysts has been compiled by von Sachtler et al. in Catalysis Reviews: Science and Engineering, 23 (1&2), 127–149 (1981).

It is also known that the silver catalysts and the reaction conditions which have proved to be favourable for ethene oxide production do not lead to comparably good results in the direct oxidation of higher olefins such as propene (U.S. Pat. No. 5,763,630, U.S. Pat. No. 5,703,254, U.S. Pat. No. 5,760,254) and maximum propene oxide selectivities of approx. 50% are achieved. Generally speaking the direct oxidations of these higher olefins with molecular oxygen in the gas phase do not take place below 200° C.—even in the presence of catalysts—and it is therefore difficult selectively to produce oxidation-sensitive oxidation products, such as epoxides, since the secondary reactions of these products often proceed more quickly than the oxidation of the olefins themselves which are used.

U.S. Pat. No. 4,833,260 describes titanium silicalite catalysts which effectively make possible the epoxidation of olefins with the oxidant hydrogen peroxide in the liquid phase. In the silicalites a small part of the lattice silicon is replaced by titanium (U.S. Pat. No. 4,410,501). The high cost of hydrogen peroxide as oxidant precludes large-scale application.

Titanium silicalite-catalyzed epoxidation with pure oxygen as oxidant is successful in the presence of a redox system consisting of alkylanthrahydroquinone and alkylanthraquinone (EP 526,945).

On titanium silicalites containing metallic platinum, propene oxidation is achieved with low yield (approx. 1–2%) and propene oxide selectivities of 60–70% in the liquid phase by means of an in-situ hydrogen peroxide formation with a gas mixture consisting of molecular oxygen and molecular hydrogen (JP-A 92/352771, WO 97/47386, WO 96/023 023). Hydrogenations which take place as secondary reactions lead to large quantities of propane as a by-product and the fact that this is a liquid phase reaction in which the epoxide which is formed is concentrated in the liquid phase makes these processes of little interest as far as industrial use is concerned.

U.S. Pat. No. 5,623,090 describes a gas phase direct oxidation of propene to propene oxide with high selectivity. This is a gold-catalyzed gas phase oxidation with molecular oxygen in the presence of hydrogen. Conventional commercial titanium dioxide, which is coated with finely dispersed gold particles, is used as the catalyst. With identical educt gases, another embodiment uses catalysts in which gold is applied to a support consisting of isolated titanium sites in a silicon dioxide matrix (WO 9800415 A1; WO 9800414 A1; WO 9800413 A1). These processes all have the disadvantage of being very expensive because of the gold content of the catalyst and are not therefore considered for an industrial use of products such as propene oxide.

The object of the present invention therefore consisted of providing a catalytic process for the oxidation of hydrocarbons which leads to improved selectivities, yields and costs.

It has surprisingly been found that this object may be achieved if hydrocarbons are caused to react in the presence of a hydrogen/oxygen mixture on a catalyst which contains silver and titanium.

The present invention thus relates to a process for the oxidation of hydrocarbons, wherein a mixture containing at least one hydrocarbon, oxygen and hydrogen is converted on a catalyst which contains silver and titanium, wherein the catalyst contains a support containing titanium and silver particles with an average particle size of 0.3 to 100 nm.

In principle the process according to the invention may be applied to all hydrocarbons. The term hydrocarbon is intended to mean saturated or unsaturated hydrocarbons such as alkanes or olefins which may also contain heteroatoms such as N, O, P or S. Hydrocarbons from which those oxidation products, the partial pressure of which is low enough consistently to remove the product from the catalyst are formed, are preferably oxidized. Unsaturated hydrocarbons with 2 to 20, preferably 2 to 10 carbon atoms, particularly ethene, propene, 1-butene, 2-butene, butadiene and pentenes and hexenes are preferred.

The catalyst containing silver contains silver particles which are preferably applied to a support.

The catalyst containing silver contains fine silver particles with average particle sizes of 0.3–100 nm, preferably 0.5–20 nm and particularly preferably 0.5 to 6 nm. The silver content in the catalyst is preferably 0.5–10 wt. %.

Pulverulent and pelletized supports are equally suitable as support materials. Amorphous high-surface support materials with surfaces >50 m$^2$/g, preferably >100 m$^2$/g, are preferred, particularly those which contain titanium such as titanyl hydrates, zinc oxide hydrate containing titanium, aluminium oxide containing titan ium, titanium dioxides (anatases) or titanium/silicon mixed compounds such as $TiO_2$—$SiO_2$ mixed oxides, titanium silicalites or molecular sieves (zeolites) in which titanium is present finely dispersed in a silicon matrix.

In principle any crystal structure of the titanium oxide may be selected although the amorphous titanium dioxide modification and anatase are preferred. The titanium oxide does not have to be present as pure component but may also be present as complex material, e.g. in combination with other oxides (e.g. titanates). According to our knowledge and without wishing to restrict the invention in any way, the titanium sites in particular which are chemically bonded to silica and/or inorganic silicates represent the catalytically active titanium sites. Furthermore we assume that in active catalysts titanium is present bonded to the silica or silicate in the form of the oxide [e.g. —Si—O—Ti(=O)—O—Si—].

The support materials containing silicon according to the invention advantageously consist of 50%, preferably of 75% and particularly preferably of >90% of the dioxide form of the silicon. In addition to silicon dioxide and silicates the support materials containing silicon according to the invention may also contain other oxides, e.g. aluminium oxide, zirconium oxide etc. Support materials containing silicon with a large specific surface and a high proportion of surface silanol groups are preferably used. The specific surface should be at least 1 m$^2$/g, preferably in the range from 25–700 m$^2$/g.

Preferred support materials containing silicon are synthetically produced porous silicon dioxides such as silica gels, precipitated silica, precipitated silica gels, silicalites or similar and mixtures thereof for example. Production methods for such synthetically produced silicas are described in "The Colloid Chemistry of Silica and Silicates (R. G. Iler, Cornell University Press, New York, USA, 1955, Chapter VI)". Examples of these silicas are pyrogenic silicas which are obtained by conversion of silicon tetrachloride or fluoride with hydrogen and oxygen (e.g. Cab-o-sils from Messrs Cabot Corporation or Aerosils from Messrs Degussa).

Crystalline alurninosilicates and silicalites, known as molecular sieves, may also be used as support materials containing silicon. Naturally occurring crystalline silicates may also be used, particularly serpentine (magnesium silicate), clay minerals such as hectorite (lithium magnesium silicate), kaolin, bentonite and mica minerals such as phlogopite (aluminium magnesium potassium silicalite) or similar materials.

The titanium oxide may be produced on support materials containing silicon in situ from titanium precursor compounds, e.g. by saturation from supernatant liquid (impregnation) and/or with an amount of solvent corresponding to the support's absorption capacity (incipient wetness), deposition precipitation, vapour desposition, and by means of the sol-gel method, but equally well by colloid methods, sputtering or vapour deposition. In the impregnations, titanium precursor compounds which can react with the surface silanol groups are advantageously used.

Suitable titanium precursor compounds as catalytic titanium species are known from the prior art, such as soluble titanium salts (e.g. titanium halides, nitrates, sulfates, titanium salts of inorganic or organic acids and titanic acid esters).

Titanium derivatives such as tetralkyl titanates with alkyl groups of $C_1$–$C_6$ such as methyl, ethyl, n-propyl, n-butyl, iso-butyl, tert.-butyl etc. or other organic titanium species such as titanyl acetyl acetonate, dicyclopentadienyl titanium dichloride are preferably used. Tetra-n-butyl orthotitanate, titanium acetyl acetonate and titanium tetrachloride are preferred titanium precursor compounds.

Titanium oxide is also produced in situ by grafting with titanocene chloride on supports containing silicon, optionally in the presence of a base. In this case the $(\eta_5$—$C_5H_2)_2TiCl_2$ reacts with terminal surface silanol groups. After grafting, drying and calcination, $(=SiO)_3TiOH$ complexes presumably form the dominant titanium species. The support materials containing titanium are coated with silver in the next step.

To increase the surface OH groups the catalysts may also be subjected to a water treatment before titanium coating. In this regard water treatment means that before titanium application the catalyst is brought into contact with liquid water or an aqueous saturated ammonium chloride solution and/or ammonium nitrate solution, or ion exchange with polyvalent cations (solution of approx. 2 t, for 3 t, approx. 2 t ions), e.g. the catalyst is suspended in the treatment medium and then dried (at 300° C. for example), or the catalyst is treated with steam at >100° C., preferably at 150 to 450° C., for 1–6 hours. Particularly preferably the catalyst is treated with steam at 200 to 450° C. for 2–5 hours. The surplus water is then removed.

To increase the surface OH groups the catalyst support may also be treated by spray impregnation with water or solutions of ammonium salts or polyvalent cations and then dried.

The silver may be applied to the support in any manner.

Catalyst preparation is preferably by the impregnation method. The amount of silver, preferably 0.5–10 wt. %, applied to the support depends on the surface, the pore structure and the chemical surface condition of the support. Amorphous and crystalline high-surface materials (>50 $m^2/g$) such as titanyl hydrates, amorphous zinc oxide hydrate containing titanium, titanium dioxides (anatases) or titanium/silicon mixed compounds such as $TiO_2$—$SiO_2$ mixed oxides, titanium silicalites or molecular sieves in which titanium sites are present in isolated form in a silicon dioxide matrix such as titanium silicalites (MFI structure; two-dimensional ten ring pore system), Ti-beta and/or Ti—Al beta (three-dimensional twelve ring pore system), Ti-ZSM-5 and/or Ti-ZSM-11 (MFI structure; ten ring channels), Ti-ZSM 12 (one-dimensional twelve ring channel system), Ti-ZSM48, Ti-MCM-41 (mesoporous) are preferably suitable as support materials for coating with silver. Titanyl hydrates and titanium/silicon mixed compounds are preferred supports. Titanyl hydrates are obtainable by hydrolysis of organic and inorganic titanium precursors (e.g. treatment of titanium ores). Hydrolysis to the titanyl hydrates may also take place in the presence of any inert support materials such as mica, silicon dioxide. Subsequent calcination of the support materials in the gas stream containing oxygen at 250 to 600° C. is particularly preferred. The support material contains immobilized silver in finely dispersed state. Titanyl hydrates with low titanium(III) contents (0.01–2%) and low sulfate contents (0.1 and 2 wt. %, preferably 0.2–1.0 wt. %) are particularly preferred. The sulfate may originate from production such as the sulfate process, or be added when the support is produced or be applied subsequently by treating the support with reagents (e.g. sulfuric acid or sodium sulfate). The activity of the catalysts which contain silver may be increased slightly (approx. 5–10%) by adding promoters. Promoters from groups 1, 2, 5 and 13 (IUPAC periodic system of the elements 1985) particularly potassium, tantalum and/or aluminium, and the lanthanides and actinides, particularly europium, lanthanum and praseodymium, of the periodic system are advantageously used. Advantageously the promoter content is 0.1–5%, preferably 0.5–3%.

The catalyst containing silver may also be produced by the deposition-precipitation method, in which an aqueous solution of an inorganic or organic silver compound (silver nitrate, sulfate, fluoride, lactate etc.) is added dropwise to an agitated suspension of the catalyst support. A solvent which contains water is preferably used. Other solvents such as alcohols may also be used. If this silver salt solution is mixed with bases (e.g. sodium carbonate, potassium carbonate, caesium carbonate or lye or alkaline earth lye) up to a pH of 7–9, silver precipitates on the support surface in the form of silver oxohydroxo complexes or as silver hydroxide/silver carbonate. To achieve a uniform deposition of ultrafine silver particles, the change in the pH may be controlled by a slow dropwise addition of this alkaline aqueous solution. It has been found that the possibility of a digestion of the precipitate with no agglomeration of the silver compounds is improved by adding a carboxylic acid or a salt (preferably magnesium or sodium citrate) during or, better still, after the neutralization of the aqueous solution with an alkaline aqueous solution. When the pH range remains at 7–9, there is virtually no reduction of the silver compound by a carbonylation. On drying, precipitated silver hydroxide or silver carbonate on the support converts into the silver oxide which decomposes and liberates oxygen when calcined above 200° C. or converts to elementary silver by reduction (e.g. hydrogen, hydrazine). The nano-scale silver particles created in this way are immobilized on the support surface in a uniform and adherent manner.

Alternatively to the deposition precipitation method, the silver particles may also be applied to the support by incipient wetness, sputtering (e.g. 5 wt. % of silver on titanyl hydrate, titanium dioxide or molecular sieves), chemical vapour deposition or from colloidal suspensions. A co-precipitation of the support and silver component is also possible. The support catalysts containing silver produced by different methods differ by their silver particle size. By the impregnation method, silver particles are obtained which are smaller than by the deposition precipitation method by a factor of 2–3.

Multiple repetition of the impregnation or deposition precipitation method with small quantities of silver (e.g. approx. 1–3 wt. % of silver in each case) is advantageous for the production of the catalyst containing silver. In the process according to the invention, catalysts are therefore preferred in which silver quantities between 1 and 4 wt. %, preferably 1–2 wt. %, were repeatedly applied to the support according to the described impregnation method after washing and drying. When used in the direct oxidation of propene with molecular oxygen in the presence of molecular hydrogen, the catalyst produced in this way according to the invention (e.g. 5 wt. % of silver on titanium dioxide) produces propene oxide with yields of 1.5–3% and propene oxide selectivities >95%. Only small quantities of ethane, methane and acetone were found as by-products (approx. 1 vol. % of by-products related to propene oxide formed).

The activity of the oxidation catalysts may decline slightly over time. These catalysts may be regenerated in the oxygen stream at conventionally 300–600° C., preferably at 300–400° C. Regeneration may also be achieved by simply washing these catalysts with water or dilute hydrogen peroxide solutions (approx. 3–10%) at room temperature or higher temperatures with subsequent drying at 150 to 250° C.

On catalyst preparation a thermal reduction of the silver compounds used may take place, e.g. during calcination at temperatures above 200° C., preferably at 300–400° C.

The process according to the invention may be carried out in the gas phase, in liquid phase or also in supercritical phase at temperatures between 20 and 200° C. and any pressure.

If the oxidation according to the invention is undertaken in liquid phase, work is advantageously carried out at a pressure of 1 to 10 bars and in the presence of solvent. Halogenated solvents such as methylene chloride are suitable as solvent in which the catalyst is suspended. Alcohols, such as methanol, ethanol, isopropanol, tert.-butanol or mixtures thereof, and water are also suitable solvents.

In the process according to the invention the catalyst used and the quantities of gas used are not restricted. In the event of a gas phase reaction the quantities of gas stream through the catalyst bed should be approx. 0.5 to 20 l/g cat.$\times$h$^{-1}$ ("space velocity").

The process according to the invention is implemented in the presence of the gases oxygen and hydrogen optionally with the addition of inert gases such as nitrogen, argon, helium or carbon dioxide. Temperatures between 30 and 70° C. (Ag/titanium dioxide systems) or 50–180° C. (Ag/titanium-containing systems) are preferred for propene oxidation. Propene oxide is obtained with a yield of 1.5–3%.

The composition of the reaction mixture, containing at least one hydrocarbon such as propene and oxygen, hydrogen and optionally an inert gas may be varied within a wide range. The process according to the invention is preferably implemented under "hydrogenation conditions", which means that only very small quantities of oxygen are used in addition to an excess of hydrogen. The following gas ratios are therefore preferably used in the process according to the invention: hydrogen/hydrocarbon/oxygen/nitrogen: 20–80 vol. %/5–30 vol. %/1–10 vol. %/0–50 vol. %. Preferably hydrogen/hydrocarbon/oxygen/nitrogen: 40–75%/7–15/3–10%/0–20%. The oxygen which is used for the reaction may be of diverse origin, e.g. pure oxygen, air or other oxygen/inert gas mixtures.

The process according to the invention provides outstanding partial oxidation selectivities at hydrocarbon conversions of 1–3%. Because of the very high selectivities, distinctly fewer by-products are formed than with conventional oxidation catalysts. The process according to the invention is particularly preferably suitable for the epoxidation of olefins, particularly for the epoxidation of propene.

Epoxide selectivities >95% (related to converted olefin) are achieved with olefin conversions of 1.5 to 3% (related to converted olefin).

The characteristics of the present invention will be illustrated in the following examples with the aid of catalyst preparations and catalytic test reactions.

EXAMPLES

Example A

Specification for Testing the Catalysts (Test Specification)

A tubular metal reactor of 10 mm internal diameter and 20 cm length, which was tempered by means of an oil thermostat, was used. The reactor was supplied with educt gases with a set of four mass flow controllers (hydrocarbon, oxygen, hydrogen, nitrogen). For the reaction 0.5 g of pulvenilent catalyst was presented at 46° C. (Ag/titanium dioxides) and/or 140° C. (Ag/TiO$_2$—SiO$_2$-mixed oxides) and 1 bar overpressure. The educt gases were metered into the reactor from above. The standard catalyst load was 2 l/g cat./h. Propene was selected by way of example as "standard hydrocarbon". To carry out the oxidation reactions, a nitrogen-enriched gas stream, denoted consistently as standard gas composition below, was selected: N$_2$/H$_2$/O$_2$/C$_3$H$_6$:15/62/10/12%. The reaction gases were analyzed quantitatively by gas chromatography. The gas chromatographic resolution of the individual reaction products took place by a combined FID/TCD method in which three capillary columns are passed through.

FID: HP-Innowax, 0.32 mm internal diameter, 60 m long, 0.25$\mu$ film thickness.

WLD: HP-Plot O, 0.32 mm internal diameter, 30 m long, 20$\mu$ film thickness

HP-Plot Molsieve 5 A, 0.32 mm internal diameter, 30 m long, 12$\mu$ film thickness.

Example 1

Oxidation of Propene

Catalyst: 2 wt. % of Ag on Titanyl Hydrate by Impregnation, Calcination.

This example illustrates a preparation according to the invention of a supported silver catalyst. To dissolve 787 mg of silver nitrate (5 wt. % of silver related to support to be used) in 100 ml of water, 11 g of titanyl hydrate (10 g of dry substance) are added at room temperature accompanied by stirring. The suspension is stirred for 1 hour at RT, the solid is separated and washed once with 20 ml of water. The moist solid is dried for 3 hours at 120° C. and then calcined in the air for 2 hours at 250° C. and 5 hours at 400° C.

A greyish-white catalyst with 2.1 wt. % of silver (EDX) is obtained. Characterization with Transition Electron Microscopy (TEM) shows nano-scale silver particles with average particle sizes in the range below 3 nm.

A propene conversion of 1.5% was achieved in a test according to the test specification, at PO selectivities of 94%.

Example 2

Oxidation of Isobutane

Catalyst: 2 wt. % of Ag on Titanyl Hydrate by Impregnation, Calcination.

The catalyst was prepared in the sane way as Example 1.
The catalyst was used for isobutane oxidation according to the test specification.

Tert.-butanol selectivities of 88% and acetic selectivities of 5% were achieved in a test according to the test specification, with an isobutane oxide conversion of 1.1%.

Example 3

Oxidation of 1-Butene

Catalyst: 2 wt. % of Ag on Titanyl Hydrate by Impregnation, Calcination.

The catalyst was prepared in the same way as Example 1.
The catalyst was used for 1-butene oxidation according to the test specification.

Butene oxide selectivities of 93% were achieved in a test according to the test specification at 1-butene conversions of 1.4%.

Example 4

Oxidation of Propene

Catalyst: 1.4 wt. % of Ag on Titanyl Hydrate by Impregnation, Calcination.

This example illustrates a preparation according to the invention of a supported silver catalyst. Preparation in the same way as Example 1 except that 475 mg of silver nitrate (3 wt. % of silver related to support to be used) in 100 ml of water were presented.

A greyish-white catalyst with 1.4 wt. % of silver (EDX) is obtained. Characterization with TEM shows nano-scale silver particles with average particle sizes below 6 nm.

The catalyst was used for propene oxidation according to the test specification.

Propene oxide selectivities of 95% were achieved in a test according to the test specification at propene conversions of 1.1%.

Example 5

Oxidation of Propene

Catalyst: 5 wt. % of Ag on Titanyl Hydrate by Deposition Precipitation, Calcination.

This example illustrates a preparation according to the invention of a supported silver catalyst. 20 g of titanyl hydrate were added at RT accompanied by stirring to dissolve 1588 mg of silver nitrate in 100 ml of water. The pH is set to 8 with a two-molar $NACO_3$ solution for silver deposition precipitation. After the pH has been set the aqueous suspension is stirred for 0.5 hours, 30 mg of magnesium citrate are added and stirring is continued for a further 2 hours at RT. The solid is separated and washed twice with 70 ml of demineralized water in each case. The moist solid is dried for 1.5 hours at 150° C. and then calcined in the air for 2 hours at 250° C. and for 5 hours at 400° C.

A greyish-white catalyst with 5 wt. % of silver (EDX) is obtained. Characterization with TEM shows nano-scale silver particles with average particle sizes from 2 to 10 nm.

The catalyst was used for propene oxidation according to the test specification.

Propene oxide selectivities of 94% were achieved in a test according to the test specification at propene conversions of 0.7%.

Example 6

Oxidation of Propene

Catalyst: 5 wt. % of Ag on Titanyl Hydrate by Sputtering, Calcination.

This example illustrates a preparation according to the invention of a supported silver catalyst.

Technical data: Leybold vapour deposition unit (A 1100); target: PK 200 (200 mm diameter); starting pressure: $1\times10^{-5}$ mbars; working pressure: $1\times10^{-3}$ mbars of argon; flask: 1 l round-bottomed flask with a 110 mm opening at an angle of 70°; rotation: 6 rpm; deposition time: 120 mins; cathode output: 110 W.

15 g of pre-dried (2 hours at 150° C.) titanyl hydrate powder are placed in the flask and sputtered with silver.

The solid is dried for 1.5 hours at 150° C. and then calcined in the air for 2 hours at 250° C. and for 5 hours at 400° C.

An anthracite-coloured catalyst with 5 wt. % of silver (EDX) is obtained. Characterization with TEM shows nano-scale silver particles with average particle sizes below 5 nm.

The catalyst was used for propene oxidation according to the test specification.

Propene oxide selectivities of 93% were achieved in a test according to the test specification at propene conversions of 1.0%.

Example 7

Oxidation of Propene

Catalyst: 2 wt. % of Ag on TS 1 by Impregnation, Calcination.

This example illustrates a preparation according to the invention of a supported silver catalyst. To dissolve 787 mg of silver nitrate (5 wt. % of silver related to support to be used) in 100 ml of water, 10 g of TS 1 are added at room temperature accompanied by stirring. The suspension is stirred for 1 hour at RT, the solid is separated and washed once with 20 ml of water. The moist solid is dried for 3 hours at 120° C. and then calcined in the air for 2 hours at 250° C. and 5 hours at 400° C.

A grey-white catalyst with 2.0 wt. % of silver (EDX) is obtained. Characterization with TEM shows nano-scale silver particles with average particle sizes below 6 nm.

The catalyst was used for propene oxidation at 140° C. according to the test specification.

Propene oxide selectivities of 94% were achieved in a test according to the test specification at propene conversions of 0.9%.

Example 8

This example describes the preparation of a catalyst support consisting of the oxides of silicon and titanium which was coated with silver particles. The catalyst support containing Si and Ti is obtained by impregnation of silica with titanocene dichloride.

20 g of pyrogenic silicon dioxide (Aerosil 200, Messrs Degussa, 200 m²/g) were suspended in a 0.5 ml ammonium nitrate solution, stirred for 2 hours at 50° C., filtered off, washed three times with 50 ml of water, dried for 2 hours at 120° C. and 3 hours at 300° C.

1568 mg of titanocene dichloride (Messrs Merck) were dissolved in 300 ml of chloroform, 10 g of dry Aerosil 380 (Messrs Degussa, pyrogenic silicon dioxide, 380 m²/g) added, stirred for 30 minutes, 1867 mg of triethylamine added, stirred for 120 minutes, suction-filtered and washed with 50 ml of chloroform, dried at 120° C. and calcined for 3 hours at 300° C. and for 1 hour at 500° C.

Coating with silver particles took place in the same way as Example 1.

A grey-white catalyst with 2 wt. % of silver (EDX) was obtained. Characterization with TEM shows nano-scale silver particles with average particle sizes in the range below 5 nm.

Propene conversions of 1.1% were achieved in a test according to the test specification at 140° C. at propene selectivities of 94%.

Example 9

This example describes the preparation of a catalyst support consisting of the oxides of silicon, aluminium and titanium which was coated with silver particles. The catalyst support containing Si and Ti is obtained by impregnation of a silicon dioxide/aluminium oxide mixed oxide with titanocene dichloride.

Preparation was in the same way as Example 8 except that a pyrogenic mixed oxide comprising silicon and aluminium was used instead of Aerosil 200 (MOX 170; Messrs Degussa, 1% $Al_2O_3$/99% $SiO_2$, 170 m²/g).

A grey-white catalyst with 2 wt. % of silver (EDX) is obtained. Characterization with TEM shows nano-scale silver particles with average particle sizes in the range below 5 nm.

Propene conversions of 1.3% were achieved in a test according to the test specification at 140° C. at propene oxide selectivities of 94%.

What is claimed is:

1. A catalyst useful for oxidizing hydrocarbons comprising:
   (a) a support material comprising titanium; and
   (b) silver particles which have an average particle size of from about 0.3 to about 100 nm;
with the proviso that the catalyst is produced by the impregnation method.

2. A method for oxidizing hydrocarbons comprising:
   oxidizing (i) a hydrocarbon with a hydrogen/oxygen mixture in the presence of a catalyst, the catalyst comprising silver particles which have an average particle size of from about 0.3 to about 100 nm and (ii) a support which comprises titanium;
with the proviso that the catalyst is produced by the impregnation method.

* * * * *